United States Patent
Andrews et al.

(10) Patent No.: US 7,745,428 B2
(45) Date of Patent: Jun. 29, 2010

(54) IMIDAZO[1,2-A]PYRIDINE HAVING ANTI-CELL-PROLIFERATION ACTIVITY

(75) Inventors: David Andrews, Macclesfield (GB); Andrew John Barker, Macclesfield (GB); Maurice Raymond Finlay, Macclesfield (GB); Clive Green, Macclesfield (GB); Clifford Jones, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/088,678

(22) PCT Filed: Sep. 29, 2006

(86) PCT No.: PCT/GB2006/003623

§ 371 (c)(1), (2), (4) Date: Aug. 4, 2008

(87) PCT Pub. No.: WO2007/036732

PCT Pub. Date: Apr. 5, 2007

(65) Prior Publication Data

US 2009/0054409 A1 Feb. 26, 2009

Related U.S. Application Data

(60) Provisional application No. 60/722,281, filed on Sep. 30, 2005.

(51) Int. Cl.
*C07D 471/04* (2006.01)
*A61K 31/437* (2006.01)

(52) U.S. Cl. ............... 514/218; 514/235.8; 514/252.14; 514/275; 540/575; 544/122; 544/295; 544/331

(58) Field of Classification Search ................. 540/575; 544/122, 295, 331; 514/218, 235.8, 252.14, 514/275
See application file for complete search history.

(56) References Cited

U.S. PATENT DOCUMENTS

| | | | |
|---|---|---|---|
| 4,659,363 A | 4/1987 | Hubele et al. | |
| 4,983,608 A | 1/1991 | Effland et al. | |
| 5,516,775 A | 5/1996 | Zimmerman et al. | |
| 5,521,184 A | 5/1996 | Zimmermann | |
| 5,610,303 A | 3/1997 | Kimura et al. | |
| 5,739,143 A | 4/1998 | Adams et al. | |
| 5,859,041 A | 1/1999 | Liverton et al. | |
| 6,432,963 B1 | 8/2002 | Hisamichi et al. | |
| 6,593,326 B1 | 7/2003 | Bradbury et al. | |
| 6,632,820 B1 | 10/2003 | Breault et al. | |
| 6,649,608 B2 | 11/2003 | Pease et al. | |
| 6,670,368 B1 | 12/2003 | Breault et al. | |
| 6,710,052 B2 | 3/2004 | Pease et al. | |
| 6,716,831 B1 | 4/2004 | Breault et al. | |
| 6,835,726 B2 | 12/2004 | Cushing et al. | |
| 6,838,464 B2 | 1/2005 | Pease et al. | |
| 6,844,341 B2 | 1/2005 | Thomas | |
| 6,855,719 B1 | 2/2005 | Thomas et al. | |
| 6,906,065 B2 | 6/2005 | Thomas | |
| 6,908,920 B2 | 6/2005 | Thomas et al. | |
| 6,939,872 B2 | 9/2005 | Newcombe et al. | |
| 6,969,714 B2 | 11/2005 | Breault et al. | |
| 7,067,522 B2 | 6/2006 | Pease et al. | |
| 7,153,964 B2 | 12/2006 | Pease et al. | |
| 7,176,212 B2 | 2/2007 | Breault et al. | |
| 2003/0144303 A1 | 7/2003 | Hawley et al. | |
| 2003/0191307 A1 | 10/2003 | Blumenkopf et al. | |
| 2004/0224966 A1 | 11/2004 | Brumby et al. | |
| 2006/0079543 A1 | 4/2006 | Sum et al. | |
| 2006/0111378 A1 | 5/2006 | Cleve et al. | |

FOREIGN PATENT DOCUMENTS

| | | |
|---|---|---|
| CA | 2231765 | 9/1998 |
| CA | 2542492 | 4/2005 |
| EP | 0135472 | 1/1989 |
| EP | 0363002 | 6/1994 |
| EP | 0379806 | 4/1996 |
| EP | 1056742 | 7/2003 |
| EP | 0945443 | 8/2003 |
| HU | 220630 | 3/2002 |
| WO | WO 91/18887 | 12/1991 |
| WO | WO 92/20642 | 11/1992 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 95/15952 | 6/1995 |
| WO | WO 96/05177 | 2/1996 |
| WO | WO 96/28427 | 9/1996 |
| WO | WO 96/40143 | 12/1996 |
| WO | WO 97/19065 | 5/1997 |
| WO | WO 97/35856 | 10/1997 |
| WO | WO 97/40017 | 10/1997 |

(Continued)

OTHER PUBLICATIONS

Banker et al., Prodrugs, Modern Pharmaceutics, Third Edition, Revised and Expanded, pp. 451 and 596, 1996.*

(Continued)

*Primary Examiner*—Deepak Rao

(57) ABSTRACT

Compounds of formula (I):

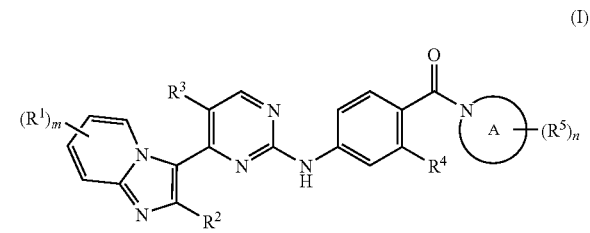

which possess cell-cycle inhibitory activity are described.

14 Claims, No Drawings

FOREIGN PATENT DOCUMENTS

| | | |
|---|---|---|
| WO | WO 97/44326 | 11/1997 |
| WO | WO 97/47618 | 12/1997 |
| WO | WO 98/11095 | 3/1998 |
| WO | WO 98/16230 | 4/1998 |
| WO | WO 98/18782 | 5/1998 |
| WO | WO 98/25619 | 6/1998 |
| WO | WO 98/33798 | 8/1998 |
| WO | WO 98/41512 | 9/1998 |
| WO | WO 98/54093 | 12/1998 |
| WO | WO 98/56788 | 12/1998 |
| WO | WO 99/01136 | 1/1999 |
| WO | WO 99/18096 | 4/1999 |
| WO | WO 99/18942 | 4/1999 |
| WO | WO 99/31073 | 6/1999 |
| WO | WO 99/32121 | 7/1999 |
| WO | WO 99/41253 | 8/1999 |
| WO | WO 99/50250 | 10/1999 |
| WO | WO 99/50251 | 10/1999 |
| WO | WO 00/12485 | 3/2000 |
| WO | WO 00/12486 | 3/2000 |
| WO | WO 00/17202 | 3/2000 |
| WO | WO 00/17203 | 3/2000 |
| WO | WO 00/21926 | 4/2000 |
| WO | WO 00/25780 | 5/2000 |
| WO | WO 00/26209 | 5/2000 |
| WO | WO 00/39101 | 7/2000 |
| WO | WO 00/44750 | 8/2000 |
| WO | WO 00/49018 | 8/2000 |
| WO | WO 00/53595 | 9/2000 |
| WO | WO 00/55161 | 9/2000 |
| WO | WO 00/59892 | 10/2000 |
| WO | WO 00/78731 | 12/2000 |
| WO | WO 01/14375 | 3/2001 |
| WO | WO 01/29009 | 4/2001 |
| WO | WO 01/30778 | 5/2001 |
| WO | WO 01/37835 | 5/2001 |
| WO | WO 01/47897 | 7/2001 |
| WO | WO 01/47921 | 7/2001 |
| WO | WO 01/60816 | 8/2001 |
| WO | WO 01/64653 | 9/2001 |
| WO | WO 01/64654 | 9/2001 |
| WO | WO 01/64655 | 9/2001 |
| WO | WO 01/64656 | 9/2001 |
| WO | WO 01/72717 | 10/2001 |
| WO | WO 02/04429 | 1/2002 |
| WO | WO 02/20512 | 3/2002 |
| WO | WO 02/46170 | 6/2002 |
| WO | WO 02/46171 | 6/2002 |
| WO | WO 02/065979 | 8/2002 |
| WO | WO 02/066480 | 8/2002 |
| WO | WO 02/066481 | 8/2002 |
| WO | WO 02/092573 | 11/2002 |
| WO | WO 02/096887 | 12/2002 |
| WO | WO 02/096888 | 12/2002 |
| WO | WO 03/007955 | 1/2003 |
| WO | WO 03/011837 | 2/2003 |
| WO | WO 03/029249 | 4/2003 |
| WO | WO 03/031446 | 4/2003 |
| WO | WO 03/037891 | 5/2003 |
| WO | WO 03/076433 | 9/2003 |
| WO | WO 03/076434 | 9/2003 |
| WO | WO 03/076435 | 9/2003 |
| WO | WO 03/076436 | 9/2003 |
| WO | 2004005282 A1 | 1/2004 |
| WO | WO 2004/005283 | 1/2004 |
| WO | WO 2004/043467 | 5/2004 |
| WO | WO 2004/043953 | 5/2004 |
| WO | WO 2004/087698 | 10/2004 |
| WO | WO 2004/087699 | 10/2004 |
| WO | WO 2004/101549 | 11/2004 |
| WO | WO 2004/101564 | 11/2004 |
| WO | WO 2005/012298 | 2/2005 |
| WO | WO 2005/037800 | 4/2005 |
| WO | 2005068452 A1 | 7/2005 |
| WO | WO 2005/075461 | 8/2005 |
| WO | WO 2005/075468 | 8/2005 |
| WO | WO 2005/113550 | 12/2005 |
| WO | WO 2005/116025 | 12/2005 |
| WO | WO 2006/034872 | 4/2006 |
| WO | WO 2006/044509 | 4/2006 |
| WO | WO 2006/050076 | 5/2006 |
| WO | WO 2006/064251 | 6/2006 |
| WO | WO 2006/075152 | 7/2006 |
| WO | WO 2006/095159 | 9/2006 |
| WO | WO 2007/015064 | 2/2007 |
| WO | 2007040436 A1 | 4/2007 |
| WO | WO 2007/040440 | 4/2007 |
| WO | WO 2007/138268 | 12/2007 |
| WO | WO 2007/138277 | 12/2007 |
| WO | WO 2007/148070 | 12/2007 |
| WO | 2008002244 A3 | 1/2008 |
| WO | 2008002245 A2 | 1/2008 |

OTHER PUBLICATIONS

Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Lu Valle et al., Cell Cycle Control in Growth Plate Chondrocytes, Frontiers in Biosciences 5, d493-503, May 2000.*
Traxler, Protein tyrosine kinase inhibitors in cancer treatment, Expert Opinion on Therapeutic Patents, 7(6), pp. 571-588, 1997.*
Anderson et al. "Imidazo[1,2-a]pyridines: A potent and selective class of cyclin-dependent kinase inhibitors identified through structure-based hybridisation" Bioorganic & Medicinal Chemistry Letters 13(18):3021-3026 (2003).
Byth et al. "Imidazo[1,2-a]pyridines. Part 2: SAR and optimisation of a potent and selective class of cyclin-dependent kinase inhibitors" Bioorganic & Medicinal Chemistry Letters 14(9): 2245-2248 (2004).
Byth et al. "Imidazo[1,2-b]pyridazines: a potent and selective class of cyclin-dependent kinase inhibitors" Bioorganic & Medicinal Chemistry Letters 14(9): 2249-2252 (2004).
Byth et al. "The cellular phenotype of AZ703, a novel selective imidazo[1,2-a]pyridine cyclin-dependent kinase inhibitor" Molecular Cancer Therapeutics 5(3):655-664 (2006).
Blain et al. "Differential Interaction of the Cyclin-dependent Kinase (Cdk) Inhibitor p27Kip1 with Cyclin A-Cdk2 and Cyclin D2-Cdk4" J. Biol. Chem. 272(41): 25863-25872 (1997).
Boschelli, D. et al. "Synthesis and tyrosine kinase inhibitory activity of a series of 2-amino-8H-pyrido[2,3-d]pyrimidines: identification of potent, selective platelet-derived growth factor receptor tyrosine kinase inhibitors" J. Med. Chem. 41(22): 4365-4377 (1998).
Deady L. et al. "Reactions of some quinazoline compounds with ethoxymethylenemalonic acid derivatives" J. Heterocyclic Chem. 26:161-168 (1989).
El-Kerdawy, M. et al. "2,4-Bis(substituted)-5-nitropyrimidines of expected diuretic act on" Egypt. J. Chem., 29(2):247-251 (1986).
Fiziol Akt Veshchestva 7:68-72 (1975) (Translation enclosed).
Ghosh, D. et al. "2,4-Bis(arylamino)-5-methylpyrimidines as antimicrobial agents" J. Med. Chem. 10: 974-975 (1967).
Ghosh, D., "2,4-Bis(arylamino)-6-methyl pyrimidines as antimicrobial agents" Chemical Abstracts, 1981, vol. 95, No. 11, Columbus, Ohio, US; Abstract No. 97712f; pp. 648; XP002109184 abstract & J. Indian Chem. Soc. 58(5):512-513. India (1981).
Schmidt, H. et al. "A convenient synthesis of 2-substituted 4-amino-5-pyrimidinecarbonitriles" J. Heterocyclic Chem. 24(5): 305-1307 (1987).
Simone "Oncology: Introduction" Cecil Textbook of Medicine, Edited by Bennett, 20th Edition, vol. 1: 1004-1010 (1996).
Volin et al. "Cell cycle implications in pathogenesis of rheumatoid arthritis" Frontiers in Bioscience 5: D594-601 (2000).

Zimmermann, J. et al. "Phenylamino-pyrimidine (PAP) derivatives: a new class of potent and selective inhibitors of protein kinase C (PKC)" Arch. Pharm. Pharm. Med. Chem. 329(7): 371-376 (1996).

Finlay et al, Imidazole piperazines: SAR and development of a potent class of cyclin-dependent kinase inhibitors with a novel mode; Bioorganic & Medicinal Chemistry Letters, 18 (2008) 4442-4446.

Anderson et al, Imidazoles: SAR and development of a potent class of cyclin-dependent kinase inhibitors; Bioorganic & Medicinal Chemistry Letters, 18 (2008) 5487-5492.

Jones et al, The discovery of AZD5597, a potent imidazole pyrimidine amide CDK inhibitor suitable for intravenous dosing; Bioorganic & Medicinal Chemistry Letters, 18 (2008) 6369-6373.

Jones et al, Imidazole pyrimidine amides as potent, orally bioavailable cyclin-dependent kinase inhibitors; Bioorganic & Medicinal Chemistry Letters, 18 (2008) 6486-6489.

* cited by examiner

IMIDAZO[1,2-A]PYRIDINE HAVING ANTI-CELL-PROLIFERATION ACTIVITY

RELATED APPLICATIONS

The present application is a U.S. National Phase Application of International Application No. PCT/GB2006/003623 (filed Sep. 29, 2006) which claims the benefit of U.S. Provisional Application No. 60/722,281 (filed Sep. 30, 2005), both of which are hereby incorporated by reference in their entirety.

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

The cell cycle is fundamental to the survival, regulation and proliferation of cells and is highly regulated to ensure that each step progresses in a timely and orderly manner. The progression of cells through the cell cycle arises from the sequential activation and de-activation of several members of the cyclin-dependent kinase (CDK) family. The activation of CDKs is dependent on their interaction with a family of intracellular proteins called cyclins. Cyclins bind to CDKs and this association is essential for CDK activity within the cell. Different cyclins are expressed and degraded at different points in the cell cycle to ensure that activation and inactivation of CDKs occurs in the correct order for progression through the cell cycle.

Moreover, CDKs appear to be downstream of a number of oncogene signalling pathways. Deregulation of CDK activity by upregulation of cyclins and/or deletion of endogenous inhibitors appears to be an important axis between mitogenic signalling pathways and proliferation of tumour cells.

Accordingly it has been recognized that an inhibitor of cell cycle kinases, particularly inhibitors of CDK1, CDK2, CDK4 and CDK6 (which operate at the G2/M, G1/S—S-G2/M and G1-S phases respectively) should be of value as an active inhibitor of cell proliferation, such as growth of mammalian cancer cells.

Tumour cells are also thought to be highly dependent on the continual transcriptional activity of RNA polymerase II to maintain appropriate levels of anti-apoptotic proteins and ensure tumour cell survival. CDK1, CDK7, CDK8 and CDK9 in particular are known to regulate the activity of RNA polymerase II through phosphorylation of the C-terminal domain of the protein. Thus, the inhibition of RNA polymerase II activity through inhibitors of these CDKs may contribute to a pro-apoptotic effect in tumour cells.

The inhibition of cell cycle kinases is expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

WO 01/14375 describes certain imidazopyridines that inhibit the effect of cell cycle kinases. WO 02/66480 describes certain imidazopyridines that are useful in the treatment of GSK3-related disorders. The present invention is based on the discovery that a novel group of imidazopyridines inhibit the effects of cell cycle kinases, particularly CDK2, and thus possess anti-cell-proliferation properties. The compounds of the present invention are not specifically disclosed in the above applications and we have identified that these compounds may possess beneficial properties in terms of one or more of their pharmacological activity (particularly as compounds which inhibit CDK2) and/or pharmacokinetic, efficacious, metabolic and toxicological profiles that make them particularly suitable for in vivo administration to a warm blooded animal, such as man.

Accordingly, the present invention provides a compound of formula (I):

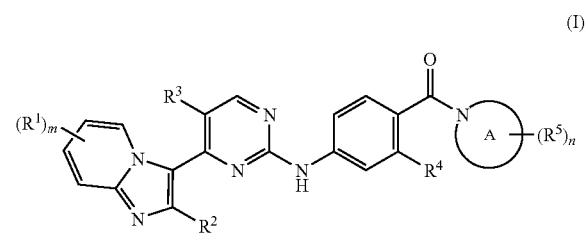

(I)

wherein:

$R^1$ is selected from halo, amino, $C_{1-3}$alkyl, $C_{1-3}$alkoxy, N—($C_{1-3}$alkyl)amino, N,N—($C_{1-3}$alkyl)$_2$-amino and a nitrogen linked 4-7 membered saturated ring which optionally contains an additional nitrogen, oxygen or sulphur atom;

m is 0-4; wherein the values of $R^1$ may be the same or different;

$R^2$ is selected from hydrogen, halo, amino, $C_{1-3}$alkyl and $C_{1-3}$alkoxy;

$R^3$ is hydrogen or halo;

$R^4$ is hydrogen, ethynyl, halo, cyano, hydroxy, amino, mesyl, trifluoromethyl, trifluoromethoxy, methyl, ethyl or methoxy;

Ring A is a nitrogen linked 4-7 membered saturated ring which optionally contains an additional nitrogen, oxygen or sulphur atom; wherein if said ring contains an additional nitrogen atom that nitrogen may be optionally substituted by $R^6$;

$R^5$ is a substituent on carbon and is selected from halo, cyano, hydroxy, trifluoromethoxy, amino, carboxy, carbamoyl, sulphamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl; wherein $R^5$ independently may be optionally substituted on carbon by one or more $R^7$; or $R^5$ is —NHR$^8$, —NR$^9$R$^{10}$ or —O—R$^{11}$;

n is 0-4; wherein the values of $R^5$ may be the same or different;

$R^6$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl and N,N—($C_{1-6}$alkyl)carbamoyl; wherein $R^6$ may be optionally substituted on carbon by one or more $R^{12}$;

$R^8$, $R^9$, $R^{10}$ and $R^{11}$ are independently selected from $C_{1-4}$alkyl, $C_{1-4}$alkanoyl, $C_{1-4}$alkylsulphonyl, $C_{2-4}$alkenylsulphonyl, $C_{2-4}$alkynylsulphonyl, $C_{1-4}$alkoxycarbonyl, carbamoyl, N—($C_{1-4}$alkyl)carbamoyl, N,N—($C_{1-4}$alkyl)carbamoyl, carbocyclyl and heterocyclyl; wherein $R^8$, $R^9$, $R^{10}$ and $R^{11}$ may be independently optionally substituted on carbon by a group selected from $R^{13}$; and wherein if said heterocyclyl contains an —NH— moiety that nitrogen may be optionally substituted by $R^{14}$;

$R^{13}$ is selected from halo, cyano, hydroxy, amino, trifluoromethyl, trifluoromethoxy, $C_{1-3}$alkyl and $C_{1-3}$alkoxy;

$R^{14}$ is selected from $C_{1-3}$alkyl, $C_{1-3}$alkanoyl, $C_{1-3}$alkylsulphonyl, $C_{1-3}$alkoxycarbonyl, carbamoyl, N—($C_{1-3}$alkyl)carbamoyl and N,N—($C_{1-3}$alkyl)carbamoyl; and $R^7$ and $R^{12}$ are independently selected from halo, cyano, hydroxy, trifluoromethoxy, trifluoromethyl, amino, carboxy, carbamoyl, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl;

or a pharmaceutically acceptable salt or an in vivo hydrolysable ester thereof.

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include methyl, ethyl, propyl, isopropyl and t-butyl. "$C_{1-3}$alkyl" includes methyl, ethyl, propyl and isopropyl. However, references to individual alkyl groups such as 'propyl' are specific for the straight chained version only and references to individual branched chain alkyl groups such as 'isopropyl' are specific for the branched chain version only. A similar convention applies to other radicals. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$— group can optionally be replaced by a —C(O)—, a ring nitrogen atom may optionally bear a $C_{1-6}$alkyl group and form a quaternary compound or a ring nitrogen and/or sulphur atom may be optionally oxidized to form the N-oxide and or the S-oxides. Examples and suitable values of the term "heterocyclyl" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. In one aspect of the invention a "heterocyclyl" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidized to form the S-oxides.

A "carbocyclyl" is a saturated, partially saturated or unsaturated, mono or bicyclic carbon ring that contains 3-12 atoms; wherein a —$CH_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl.

A "nitrogen linked 4-7 membered saturated ring which optionally contains an additional nitrogen, oxygen or sulphur atom" is a saturated monocyclic ring containing 4-7 atoms linked to formula (I) via a nitrogen atom contained in the ring, the ring optionally contains an additional heteroatom selected from nitrogen, sulphur or oxygen, wherein a —$CH_2$—group can optionally be replaced by a —C(O)—, and the optional sulphur atom may be optionally oxidized to form the S-oxides. A "nitrogen linked 5 or 6 membered saturated ring which optionally contains an additional nitrogen, oxygen or sulphur atom" is defined as for a "nitrogen linked 4-7 membered saturated ring which optionally contains an additional nitrogen, oxygen or sulphur atom" but wherein the ring has only 5 or 6 atoms. Suitable values of a "nitrogen linked 4-7 membered saturated ring which optionally contains an additional nitrogen, oxygen or sulphur atom" include piperidinyl, morpholino, pyrrolidino and piperazinyl. A further suitable example is homopiperazinyl.

Examples of "$C_{1-6}$alkoxycarbonyl" and "$C_{1-4}$alkoxycarbonyl" include methoxycarbonyl, ethoxycarbonyl, n- and t-butoxycarbonyl. Examples of "$C_{1-3}$alkoxycarbonyl" include methoxycarbonyl and ethoxycarbonyl. Examples of "$C_{1-3}$alkoxy" include methoxy, ethoxy and propoxy. Examples of "$C_{1-6}$alkylS(O)$_a$ wherein a is 0 to 2" include methylthio, ethylthio, methylsulphinyl, ethylsulphinyl, mesyl and ethylsulphonyl. Examples of "$C_{1-6}$alkanoyl", "$C_{1-4}$alkanoyl" and "$C_{1-3}$alkanoyl" include propionyl and acetyl. Examples of "$C_{2-6}$alkenyl" are vinyl, alkyl and 1-propenyl. Examples of "$C_{2-6}$alkynyl" are ethynyl, 1-propynyl and 2-propynyl. Examples of "N—($C_{1-6}$alkyl)sulphamoyl" are N-(methyl)sulphamoyl and N-(ethyl)sulphamoyl. Examples of "N,N—($C_{1-6}$alkyl)$_2$sulphamoyl" are N,N-(dimethyl)sulphamoyl and N-(methyl)-N-(ethyl)sulphamoyl. Examples of "N—($C_{1-6}$alkyl)carbamoyl", "N—($C_{1-4}$alkyl)carbamoyl" and "N—($C_{1-3}$alkyl)carbamoyl" are methylaminocarbonyl and ethylaminocarbonyl. Examples of "N,N—($C_{1-6}$alkyl)$_2$-carbamoyl", "N,N—($C_{1-4}$alkyl)$_2$-carbamoyl" and "N,N—($C_{1-3}$alkyl)$_2$-carbamoyl" are dimethylaminocarbonyl and methylethylaminocarbonyl. Examples of "$C_{1-4}$alkylsulphonyl" and include methylsulphonyl, isopropylsulphonyl and t-butylsulphonyl. Examples of "$C_{1-3}$alkylsulphonyl" and include methylsulphonyl and isopropylsulphonyl. Examples of "$C_{1-4}$alkenylsulphonyl" include ethenylsulphonyl and allylsulphonyl. Examples of "$C_{1-4}$alkynylsulphonyl" include ethynylsulphonyl and propynylsulphonyl. Examples of "N—($C_{1-3}$alkyl)amino" included methylamino and ethylamino. Examples of "N,N—($C_{1-3}$alkyl)$_2$-amino" include methylethylamino and dimethylamino.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

An in vivo hydrolysable ester of a compound of the formula (I) containing carboxy or hydroxy group is, for example, a pharmaceutically acceptable ester which is hydrolyzed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity.

It is also to be understood that certain compounds of the formula (I) can exist in solvated as well as unsolvated forms such as, for example, hydrated forms. It is to be understood that the invention encompasses all such solvated forms which possess CDK inhibitory activity.

Particular values of variable groups are as follows. Such values may be used where appropriate with any of the definitions, claims or embodiments defined hereinbefore or hereinafter.

m is 0.
$R^2$ is selected from hydrogen or $C_{1-3}$alkyl.
$R^2$ is selected from hydrogen or methyl.
$R^2$ is methyl.
$R^2$ is hydrogen.
$R^3$ is hydrogen.
$R^3$ is halo.
$R^3$ is fluoro.
$R^4$ is hydrogen, halo or methyl.
$R^4$ is hydrogen, fluoro or methyl.
Ring A is a nitrogen linked 5-7 membered saturated ring which optionally contains an additional nitrogen or oxygen atom; wherein if said ring contains an additional nitrogen atom that nitrogen may be optionally substituted by $R^6$; wherein $R^6$ is $C_{1-6}$alkyl.
Ring A is a nitrogen linked 5 or 6 membered saturated ring which optionally contains an additional nitrogen or oxygen atom; wherein if said ring contains an additional nitrogen atom that nitrogen may be optionally substituted by $R^6$; wherein $R^6$ is $C_{1-6}$alkyl.
Ring A is pyrrolidin-1-yl, piperazin-1-yl, homopiperazin-1-yl or morpholino; wherein said piperazin-1-yl or homopiperazin-1-yl may be optionally substituted on nitrogen by $R^6$; wherein $R^6$ is methyl or isopropyl.
Ring A is pyrrolidin-1-yl, piperazin-1-yl or morpholino; wherein said piperazin-1-yl may be optionally substituted on nitrogen by $R^6$; wherein $R^6$ is methyl.
Ring A is pyrrolidin-1-yl, 4-methylpiperazin-1-yl, 4-methylhomopiperazin-1-yl or 4-isopropylhomopiperazin-1-yl or morpholino.
Ring A is pyrrolidin-1-yl, 4-methylpiperazin-1-yl or morpholino.
$R^5$ is a substituent on carbon and is selected from —$NR^9R^{10}$; wherein $R^9$ and $R^{10}$ are independently selected from $C_{1-4}$alkyl.
$R^5$ is a substituent on carbon and is selected from —$NR^9R^{10}$; wherein $R^9$ and $R^{10}$ are independently selected from methyl.
$R^5$ is a substituent on carbon and is dimethylamino.
n is 0.
n is 1.
n is 0 or 1.

Therefore in a further aspect of the invention there is provided a compound of formula (I) (as depicted above) wherein:
m is 0;
$R^2$ is selected from hydrogen or $C_{1-3}$alkyl;
$R^3$ is hydrogen;
$R^4$ is hydrogen, halo or methyl;
Ring A is a nitrogen linked 5-7 membered saturated ring which optionally contains an additional nitrogen or oxygen atom; wherein if said ring contains an additional nitrogen atom that nitrogen may be optionally substituted by $R^6$; wherein $R^6$ is $C_{1-6}$alkyl.
$R^5$ is a substituent on carbon and is selected from —$NR^9R^{10}$; wherein $R^9$ and $R^{10}$ are independently selected from $C_{1-4}$alkyl;
n is 0 or 1;

or a pharmaceutically acceptable salt or an in vivo hydrolysable ester thereof.

Therefore in a further aspect of the invention there is provided a compound of formula (I) (as depicted above) wherein:
m is 0;
$R^2$ is hydrogen;
$R^3$ is hydrogen;
$R^4$ is hydrogen, halo or methyl;
Ring A is a nitrogen linked 5 or 6 membered saturated ring which optionally contains an additional nitrogen or oxygen atom; wherein if said ring contains an additional nitrogen atom that nitrogen may be optionally substituted by $R^6$; wherein $R^6$ is $C_{1-6}$alkyl;
$R^5$ is a substituent on carbon and is selected from —$NR^9R^{10}$; wherein $R^9$ and $R^{10}$ are independently selected from $C_{1-4}$alkyl;
n is 0 or 1;

or a pharmaceutically acceptable salt or an in vivo hydrolysable ester thereof.

Therefore in a further aspect of the invention there is provided a compound of formula (I) (as depicted above) wherein
m is 0;
$R^2$ is selected from hydrogen or methyl;
$R^3$ is hydrogen;
$R^4$ is hydrogen, fluoro or methyl;
Ring A is pyrrolidin-1-yl, 4-methylpiperazin-1-yl, 4-methylhomopiperazin-1-yl or 4-isopropylhomopiperazin-1-yl or morpholino;
$R^5$ is a substituent on carbon and is dimethylamino;
n is 0 or 1;

or a pharmaceutically acceptable salt or an in vivo hydrolysable ester thereof.

Therefore in a further aspect of the invention there is provided a compound of formula (I) (as depicted above) wherein m is 0;

$R^2$ is hydrogen;

$R^3$ is hydrogen;

$R^4$ is hydrogen, fluoro or methyl;

Ring A is pyrrolidin-1-yl, 4-methylpiperazin-1-yl or morpholino;

$R^5$ is a substituent on carbon and is dimethylamino;

n is 0 or 1;

or a pharmaceutically acceptable salt or an in vivo hydrolysable ester thereof.

In another aspect of the invention, preferred compounds of the invention are any one of the Examples or a pharmaceutically acceptable salt or an in vivo hydrolysable ester thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein variable groups are, unless otherwise specified, as defined in formula (I)) comprises of:

Process a) reaction of a pyrimidine of formula (II):

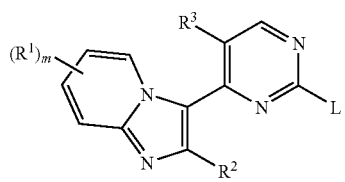

wherein L is a displaceable group; with an aniline of formula (III):

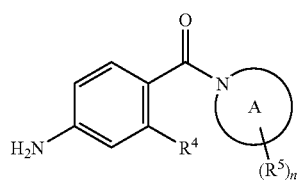

or

Process b) reacting a compound of formula (IV):

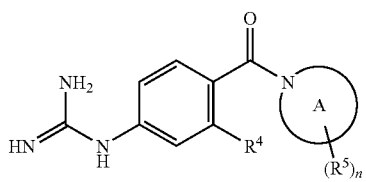

with a compound of formula (V):

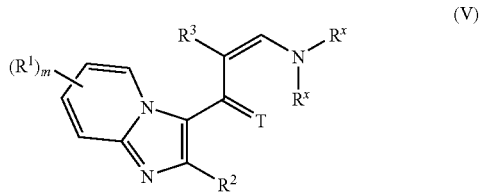

wherein T is O or S; $R^x$ may be the same or different and is selected from $C_{1-6}$alkyl; or Process c) reacting an acid of formula (VI):

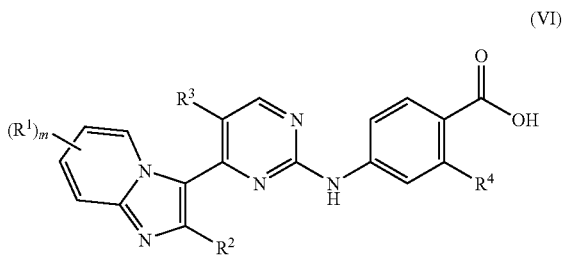

or an activated acid derivative thereof; with an amine of formula (VII):

or

Process d) for compounds of formula (I); reacting a pyrimidine of formula (VIII):

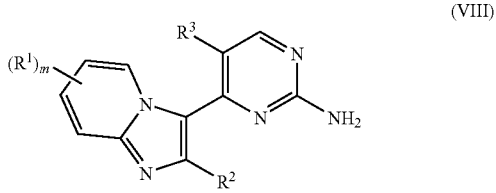

with a compound of formula (IX):

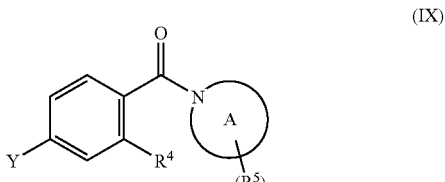

where Y is a displaceable group;

and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

Y is a displaceable group, suitable values for Y are for example, a halogeno or sulphonyloxy group, for example a bromo, iodo or trifluoromethanesulphonytoxy group. Preferably Y is iodo.

Specific reaction conditions for the above reactions are as follows.

Process a) Pyrimidines of formula (II) and anilines of formula (III) may be reacted together:
i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or
ii) under standard Buchwald conditions (for example see *J. Am. Chem. Soc.*, 118, 7215; *J. Am. Chem. Soc.*, 119, 8451; *J. Org Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) where L is chloro may be prepared according to Scheme 1:

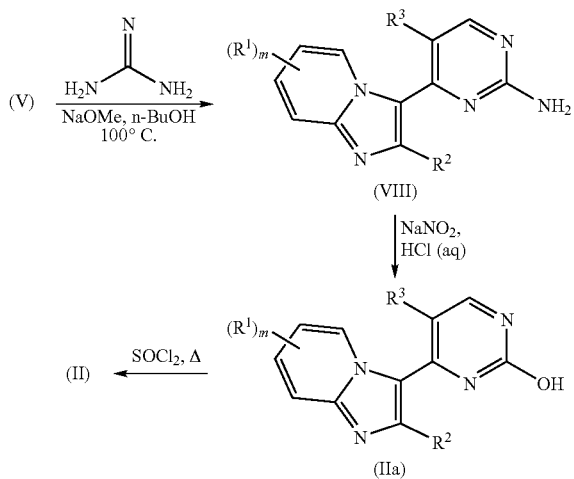

Anilines of formula (III) are commercially available compounds, or they are known in the literature, or they are prepared by standard processes known in the art.

Process b) Compounds of formula (IV) and compounds of formula (V) are reacted together in a suitable solvent such as N-methylpyrrolidinone or butanol at a temperature in the range of 100-200° C., preferably in the range of 150-170° C. The reaction is preferably conducted in the presence of a suitable base such as, for example, sodium hydride, sodium methoxide or potassium carbonate.

Compounds of formula (V) may be prepared according to Scheme 2:

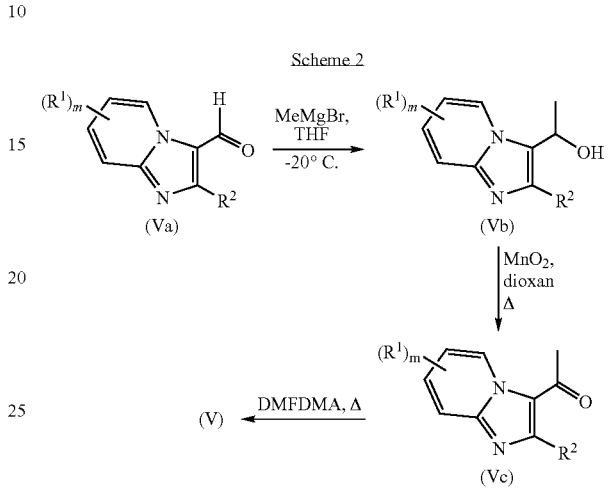

Compounds of formula (IV) and (Va) are commercially available compounds, or they are known in the literature, or they are prepared by standard processes known in the art.

Process c) Acids and amines may be coupled together in the presence of a suitable coupling reagent. Standard peptide coupling reagents known in the art can be employed as suitable coupling reagents, or for example carbonyldiimidazole and dicyclohexyl-carbodiimide, optionally in the presence of a catalyst such as dimethylaminopyridine or 4-pyrrolidinopyridine, optionally in the presence of a base for Example triethylamine, pyridine, or 2,6-di-allkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Compounds of formula (VI) may be prepared by adapting Process a), b) or c).

Amines of formula (VII) are commercially available compounds, or they are known in the literature, or they are prepared by standard processes known in the art.

Process d) Compounds of formula (VIII) and amines of formula (IX) may be reacted together under standard Buchwald conditions as described in Process a.

The synthesis of compounds of formula (VIII) is described in Scheme 1.

Compounds of formula (IX) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) wider Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedure set out below:

Assay

The following abbreviations have been used:

HEPES is N-[2-Hydroxyethyl]piperazine-N'-[2-ethanesulfonic acid]

DTT is Dithiothreitol

PMSF is Phenylmethylsulphonyl fluoride

The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma protein; GST-Rb). In each well was placed the compound to be tested (diluted in DMSO and water to correct concentrations) and in control wells either roscovitine as an inhibitor control or DMSO as a positive control.

Approximately 0.2 µl of CDK2/Cyclin E partially-purified enzyme (amount dependent on enzyme activity) diluted in 25 µl incubation buffer was added to each well then 20 µl of GST-Rb/ATP/ATP33 mixture (containing 0.5 µg GST-Rb and 0.2 µM ATP and 0.14 µCi[γ-33-P]-Adenosine Triphosphate in incubation buffer), and the resulting mixture shaken gently, then incubated at room temperature for 60 minutes.

To each well was then added 150 µL stop solution containing (0.88 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH7.5, 10 mM $MnCl_2$, 1 mM DTT, 100 µM Sodium vanadate, 100 µM NaF, 10 mM Sodium Glycerophosphate, BSA (1 mg/ml final).

Test Substrate

In this assay only part of the retinoblastoma protein (Science 1987 Mar. 13;235(4794):1394-1399; Lee W. H., Bookstein R., Hong F., Young L. J., Shew J. Y., Lee E. Y.) was used, fused to a GST tag. PCR of retinoblastoma gene encoding amino acids 379-928 (obtained from retinoblastoma plasmid ATCC pLRbRNL) was performed, and the sequence cloned into pGEx 2T fusion vector (Smith D. B. and Johnson, K. S. Gene 67, 31 (1988); which contained a tac promoter for inducible expression, internal lac $I_q$ gene for use in any E. Coli host, and a coding region for thrombin cleavage—obtained from Pharmacia Biotech) which was used to amplify amino acids 792-928. This sequence was again cloned into pGEx 2T.

The retinoblastoma 792-928 sequence so obtained was expressed in *E. Coli* (BL21 (DE3) pLysS cells) using standard inducible expression techniques, and purified as follows.

*E. coli* paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgI2, 1 mM DTT, 1 mM PMSF, 1 ug/ml leupeptin, 1 ug/ml aprotinin and 1 ug/ml pepstatin) the protein was eluted with 50mM reduced glutathione in kinase buffer. Fractions containing GST-Rb (792-927) were pooled and dialysed overnight against kinase buffer. The final product was analysed by Sodium Dodeca Sulfate (SDS) PAGE (Polyacrylamide gel) using 8-16% Tris-Glycine gels (Novex, San Diego, USA).

CDK and Cyclin E

The open reading frames of CDK2 and Cyclin E were isolated by reverse transcriptase-PCR using HeLa cell and activated T cell mRNA as a template and cloned into the insect expression vector pVL1393 (obtained from Invitrogen 1995 catalogue number: V1392-20). CDK2 and cyclin E were then dually expressed [using a standard virus Baculogold co-infection technique] in the insect SF21 cell system (*Spodoptera Frugiperda* cells derived from ovarian tissue of the Fall Army Worm—commercially available).

Example Production of Cyclin E/CDK2

The following Example provides details of the production of Cyclin E/CDK2 in SF21 cells (in TC100+10% FBS(TCS)+ 0.2% Pluronic) having dual infection MOI 3 for each virus of Cyclin E & CDK2.

SF21 cells grown in a roller bottle culture to 2.33×10$^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

The viruses were mixed together before addition to the cultures, and the cultures returned to the roller rig 28° C.

After 2 days (48 hrs.) post infection the 5 Litres of culture was harvested. The total cell count at harvest was 1.58×10E6 cells/ml.(99% viable). The cells were spun out at 2500 rpm, 30 mins., 4° C. in Heraeus Omnifuge 2.0 RS in 250 ml. lots. The supernatant was discarded.

Partial Co-Purification of Cdk2 and Cyclin E

Sf21 cells were resuspended in lysis buffer (50 mM Tris pH 8.2, 10 mM MgCl$_2$, 1 mM DTT, 10 mM glycerophosphate, 0.1mM sodium orthovanadate, 0.1mM NaF, 1 mM PMSF, 1 ug/ml leupeptin and 1 ug/ml aprotinin) and homogenised for 2 minutes in a 10 ml Dounce homgeniser. After centrifugation, the supernatant was loaded onto a Poros HQ/M 1.4/100 anion exchange column (PE Biosystems, Hertford, UK). Cdk2 and Cyclin E were coeluted at the beginning of a 0-1 M NaCl gradient (run in lysis buffer minus protease inhibitors) over 20 column volumes. Co-elution was checked by western blot using both anti-Cdk2 and anti-Cyclin E antibodies (Santa Cruz Biotechnology, California, US).

By analogy, assays designed to assess inhibition of CDK1 and CDK4 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

Although the pharmacological properties of the compounds of the formula (I) vary with structural change, in general activity possessed by compounds of the formula (I) may be demonstrated at $IC_{50}$ concentrations or doses in the range 250 µM to 1 nM.

When tested in the above in-vitro assay the CDK2 inhibitory activity of Example 2 CDK2 enzyme 0.09 µM.

In Vivo Activity

The in vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R.(1989) Status of the NCI preclinical antitumour drug discovery screen. Prin. Prac Oncol 10:1-12). Thus, the following details are provided of measuring inhibition of cell growth:—

Cells may be plated in appropriate medium in a volume of 100 ml in 96 well plates; media may be Dulbecco's Modified Eagle media for MCF-7, SK-UT-1B and SK-UT-1. The cells may be allowed to attach overnight, then inhibitor compounds added at various concentrations in a maximum concentration of 1% DMSO (v/v). A control plate may be assayed to give a value for cells before dosing. Cells may be incubated at 37° C., (5% $CO_2$) for three days.

At the end of three days TCA may be added to the plates to a final concentration of 16% (v/v). Plates may be incubated at 4° C. for 1 hour, the supernatant removed and the plates washed in tap water. After drying, 100 ml SRB dye (0.4% SRB in 1% acetic acid) may be added for 30 minutes at 37° C. Excess SRB may be removed and the plates washed in 1% acetic acid. The SRB bound to protein may be solubilised in 10 mM Tris pH7.5 and shaken for 30 minutes at room temperature. The ODs may be read at 540 nm, and the concentration of inhibitor causing 50% inhibition of growth determined from a semi-log plot of inhibitor concentration versus absorbance. The concentration of compound that reduced the optical density to below that obtained when the cells were plated at the start of the experiment should give the value for toxicity.

Typical $IC_{50}$ values for compounds of the invention when tested in the SRB assay should be in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative and potentially apoptotic effect mediated alone or in part by the inhibition of CDKs. Particularly, an inhibitory effect is produced by preventing entry into or progression through the S phase by inhibition of CDK2, CDK4 and/or CDK6, especially CDK2 and entry into or progression through M phase by inhibition of CDK1. Apoptotic effects may also be envisaged through down-regulation of RNA polymerase II activity by inhibition of CDK1, CDK7, CDK8 and in particular, CDK9. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament.

In a further aspect of the invention there is provided the use of a compound of the formula (I), or a pharmaceutically acceptable salt or in vivo hydrolysable ester thereof, as defined hereinbefore in the manufacture of a medicament for use in the production of a cell cycle inhibitory effect.

In one aspect of the invention, where a cell cycle inhibitory effect is referred to this refers to inhibition of CDK1. In a further aspect of the invention, this refers to inhibition of CDK2. In a further aspect of the invention, this refers to inhibition of CDK4. In a further aspect of the invention, this refers to inhibition of CDK5. In a further aspect of the invention, this refers to inhibition of CDK6. In a further aspect of the invention, this refers to inhibition of CDK7. In a further aspect of the invention, this refers to inhibition of CDK8. In a further aspect of the invention, this refers to inhibition of CDK9.

In a further aspect of the invention there is provided the use of a compound of the formula (I), or a pharmaceutically acceptable salt or in vivo hydrolysable ester thereof, as defined hereinbefore in the manufacture of a medicament for use in the production of an anti-cell-proliferation effect.

In a further aspect of the invention there is provided the use of a compound of the formula (I), or a pharmaceutically acceptable salt or in vivo hydrolysable ester thereof, as defined hereinbefore in the manufacture of a medicament for use in the production of a CDK2 inhibitory effect.

In a further aspect of the invention there is provided the use of a compound of the formula (I), or a pharmaceutically acceptable salt or in vivo hydrolysable ester thereof, as defined hereinbefore in the manufacture of a medicament for use in the treatment of cancer.

In a further aspect of the invention there is provided the use of a compound of the formula (I), or a pharmaceutically acceptable salt or in vivo hydrolysable ester thereof, as defined hereinbefore in the manufacture of a medicament for use in the treatment of leukaemia or lymphoid malignancies or cancer of the breast, lung, colon, rectum, stomach, liver, kidney, prostate, bladder, pancreas, vulva, skin or ovary.

According to a further feature of the invention, there is provided the use of a compound of the formula (I), or a pharmaceutically acceptable salt or in vivo hydrolysable ester thereof, as defined herein before in the manufacture of a medicament for use in the treatment of cancer, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

In a further aspect of the invention there is provided a method of producing a cell cycle inhibitory effect, in a warm-blooded animal in need of such treatment, which comprises administering to said animal an effective amount of a compound of formula (I) or a pharmaceutically acceptable salt or in vivo hydrolysable ester thereof, as defined herein before.

In a further aspect of the invention there is provided a method of producing an anti-cell-proliferation effect, in a warm-blooded animal in need of such treatment, which comprises administering to said animal an effective amount of a compound of formula (I) or a pharmaceutically acceptable salt or in vivo hydrolysable ester thereof, as defined herein before.

In a further aspect of the invention there is provided a method of producing a CDK2 inhibitory effect, in a warm-blooded animal in need of such treatment, which comprises administering to said animal an effective amount of a compound of formula (I) or a pharmaceutically acceptable salt or in vivo hydrolysable ester thereof, as defined herein before.

In a further aspect of the invention there is provided a method of treating cancer, in a warm-blooded animal in need of such treatment, which comprises administering to said animal an effective amount of a compound of formula (I) or a pharmaceutically acceptable salt or in vivo hydrolysable ester thereof, as defined herein before.

In a further aspect of the invention there is provided a method of treating leukaemia or lymphoid malignancies or cancer of the breast, lung, colon, rectum, stomach, liver, kidney, prostate, bladder, pancreas, vulva, skin or ovary, in a warm-blooded animal in need of such treatment, which comprises administering to said animal an effective amount of a compound of formula (I) or a pharmaceutically acceptable salt or in vivo hydrolysable ester thereof, as defined herein before.

In a further aspect of the invention there is provided a method of treating cancer, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal in need of such treatment, which comprises administering to said animal an effective amount of a compound of formula (I) or a pharmaceutically acceptable salt or in vivo hydrolysable ester thereof, as defined herein before.

In a further aspect of the invention there is provided a pharmaceutical composition which comprises a compound of the formula (I), or a pharmaceutically acceptable salt or in vivo hydrolysable ester thereof, as defined herein before and a pharmaceutically-acceptable diluent or carrier.

In a further aspect of the invention there is provided a pharmaceutical composition which comprises a compound of the formula (I), or a pharmaceutically acceptable salt or in vivo hydrolysable ester thereof, as defined herein before and a pharmaceutically-acceptable diluent or carrier for use as a medicament.

In a further aspect of the invention there is provided a pharmaceutical composition which comprises a compound of the formula (I), or a pharmaceutically acceptable salt or in vivo hydrolysable ester thereof, as defined herein before and a pharmaceutically-acceptable diluent or carrier for use in the production of a cell cycle inhibitory effect.

In a further aspect of the invention there is provided a pharmaceutical composition which comprises a compound of the formula (I), or a pharmaceutically acceptable salt or in vivo hydrolysable ester thereof, as defined herein before and a pharmaceutically-acceptable diluent or carrier for use in the production of an anti-cell-proliferation effect.

In a further aspect of the invention there is provided a pharmaceutical composition which comprises a compound of the formula (I), or a pharmaceutically acceptable salt or in vivo hydrolysable ester thereof, as defined herein before and a pharmaceutically-acceptable diluent or carrier for use in the production of a CDK2 inhibitory effect.

In a further aspect of the invention there is provided a pharmaceutical composition which comprises a compound of the formula (I), or a pharmaceutically acceptable salt or in vivo hydrolysable ester thereof, as defined herein before and a pharmaceutically-acceptable diluent or carrier for use in the treatment of cancer.

In a further aspect of the invention there is provided a pharmaceutical composition which comprises a compound of the formula (I), or a pharmaceutically acceptable salt or in vivo hydrolysable ester thereof, as defined herein before and a pharmaceutically-acceptable diluent or carrier for use in the treatment of leukaemia or lymphoid malignancies or cancer of the breast, lung, colon, rectum, stomach, liver, kidney, prostate, bladder, pancreas, vulva, skin or ovary.

In a further aspect of the invention there is provided a pharmaceutical composition which comprises a compound of the formula (I), or a pharmaceutically acceptable salt or in vivo hydrolysable ester thereof, as defined herein before and a pharmaceutically-acceptable diluent or carrier for use in the treatment of cancer, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

In a further aspect of the invention there is provided the use of a compound of the formula (I), or a pharmaceutically acceptable salt or in vivo hydrolysable ester thereof, as defined hereinbefore, in the production of a cell cycle inhibitory effect.

In a further aspect of the invention there is provided the use of a compound of the formula (I), or a pharmaceutically acceptable salt or in vivo hydrolysable ester thereof, as defined hereinbefore, in the production of an anti-cell-proliferation effect.

In a further aspect of the invention there is provided the use of a compound of the formula (I), or a pharmaceutically acceptable salt or in vivo hydrolysable ester thereof, as defined hereinbefore, in the production of a CDK2 inhibitory effect.

In a further aspect of the invention there is provided the use of a compound of the formula (I), or a pharmaceutically acceptable salt or in vivo hydrolysable ester thereof, as defined hereinbefore, in the treatment of cancer.

In a further aspect of the invention there is provided the use of a compound of the formula (I), or a pharmaceutically acceptable salt or in vivo hydrolysable ester thereof, as defined hereinbefore in the treatment of leukaemia or lymphoid malignancies or cancer of the breast, lung, colon, rectum, stomach, liver, kidney, prostate, bladder, pancreas, vulva, skin or ovary.

According to a further feature of the invention, there is provided the use of a compound of the formula (I), or a pharmaceutically acceptable salt or in vivo hydrolysable ester thereof, as defined herein before in the treatment of cancer, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Preventing cells from entering DNA synthesis by inhibition of essential S-phase initiating activities such as CDK2 initiation may also be useful in protecting normal cells of the body from toxicity of cycle-specific pharmaceutical agents. Inhibition of CDK2 or 4 will prevent progression into the cell cycle in normal cells which could limit the toxicity of cycle-specific pharmaceutical agents which act in S-phase, G2 or mitosis. Such protection may result in the prevention of hair loss normally associated with these agents.

Therefore in a further aspect of the invention there is provided a compound of formula (I) as defined above or a pharmaceutically acceptable salt or in vivo hydrolysable ester thereof for use as a cell protective agent.

Therefore in a further aspect of the invention there is provided a compound of formula (I) as defined above or a pharmaceutically acceptable salt or in vivo hydrolysable ester thereof for use in preventing hair loss arising from the treatment of malignant conditions with pharmaceutical agents.

Examples of pharmaceutical agents for treating malignant conditions that are known to cause hair loss include alkylating agents such as ifosfamide and cyclophosphamide; antimetabolites such as methotrexate, 5-fluorouracil, gemcitabine and cytarabine; vinca alkaloids and analogues such as vincristine, vinbalstine, vindesine, vinorelbine; taxanes such as paclitaxel and docetaxel; topoisomerase I inhibitors such as irintotecan and topotecan; cytotoxic antibiotics such as doxorubicin, daunorubicin, mitoxantrone, actinomycin-D and mitomycin; and others such as etoposide and tretinoin.

In another aspect of the invention, the compound of formula (I), or a pharmaceutically acceptable salt or in vivo hydrolysable ester thereof, may be administered in association with a one or more of the above pharmaceutical agents. In this instance the compound of formula (I) may be administered by systemic or non systemic means. Particularly the compound of formula (I) my may administered by non-systemic means, for example topical administration.

Therefore in an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof.

In an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof in simultaneous, sequential or separate administration with an effective amount of said pharmaceutical agent.

According to a further aspect of the invention there is provided a pharmaceutical composition for use in preventing hair loss arising from the treatment of malignant conditions with pharmaceutical agents which comprises a compound of formula (I), or a pharmaceutically acceptable salt or in vivo hydrolysable ester thereof, and said pharmaceutical agent, in association with a pharmaceutically acceptable diluent or carrier.

According to a further aspect of the present invention there is provided a kit comprising a compound of formula (I), or a pharmaceutically acceptable salt or in vivo hydrolysable ester thereof, and a pharmaceutical agent for treating malignant conditions that is known to cause hair loss.

According to a further aspect of the present invention there is provided a kit comprising:
a) a compound of formula (I), or a pharmaceutically acceptable salt or in vivo hydrolysable ester thereof, in a first unit dosage form;
b) a pharmaceutical agent for treating malignant conditions that is known to cause hair loss; in a second unit dosage form; and
c) container means for containing said first and second dosage forms.

According to another feature of the invention there is provided the use of a compound of the formula (I), or a pharmaceutically acceptable salt or in vivo hydrolysable ester thereof, in the manufacture of a medicament for the prevention of hair loss during treatment of malignant conditions with pharmaceutical agents.

According to a further aspect of the present invention there is provided a combination treatment for the prevention of hair loss comprising the administration of an effective amount of a compound of the formula (I), or a pharmaceutically acceptable salt or in vivo hydrolysable ester thereof, optionally together with a pharmaceutically acceptable diluent or carrier, with the simultaneous, sequential or separate administration of an effective amount of a pharmaceutical agent for treatment of malignant conditions to a warm-blooded animal, such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;
(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and
(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non limiting examples in which, unless stated otherwise:
(i) temperatures are given in degrees Celsius (° C.); operations were carried out at room or ambient temperature, that is, at a temperature in the range of 18-25° C.;
(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and reaction times are given for illustration only;
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated;
(viii) chemical symbols have their usual meanings; SI units and symbols are used;
(ix) solvent ratios are given in volume:volume (v/v) terms; and
(x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(MH)^+$;
(xi) unless stated otherwise compounds containing an asymmetrically substituted carbon and/or sulphur atom have not been resolved;
(xii) where a synthesis is described as being analogous to that described in a previous example the amounts used are the millimolar ratio equivalents to those used in the previous example; and
(xvi) the following abbreviations have been used:

| | |
|---|---|
| MeOH | methanol; |
| DCM | dichloromethane; |
| DMSO | dimethylsulphoxide; |
| EDTA | ethylenediaminetetraacetic acid; |
| HBTU | O-benzotriazol-1-yl-N,N,N',N'-tetramethyluronium hexafluorophosphate; |
| DIPEA | N,N-diisopropylethylamine; |
| RPHPLC | reverse phase high performance liquid chromatography; and |
| Xanthphos | 9,9-dimethyl-4,5-bis(diphenylphosphino)xanthene. |

Example 1

[4-(4-Imidazo[1,2-α]pyridin-3-yl-pyrimidin-2-ylamino)-phenyl]-morpholin-4-yl-methanone 4-Imidazo[1,2-α]pyridin-3-yl-pyrimidin-2-ylamine (Bioorganic & Medicinal Chemistry Letters 2004, 14(9), 2245-2248) (0.20 g, 0.95 mmol), palladium acetate (9 mg, 0.038 mmol), Xanthphos (33 mg, 0.057 mmol), caesium carbonate (0.46 g, 1.4 mmol) and (4-iodo-phenyl)-morpholin-4-yl-methanone (Method 16a in WO 05/044814) (330 mg, 1.05 mmol) were added to dioxane (7 ml) under a inert atmosphere and heated at reflux for 6 hours. Purification on silica using 0-10% MeOH in DCM as eluent gave the title compound as a colourless foam. Further purification was achieved using RPHPLC to give a colourless foam (239 mg, 63%); $^1$H NMR (400.132 MHz) 10.13 (d, 1H), 9.89 (s, 1H), 8.64 (s, 1H), 8.48 (d, 1H), 7.85 (d, 2H), 7.79 (d, 1H), 7.52 (t, 1H), 7.46 (d, 1H), 7.43 (d, 2H), 7.16 (t, 1H), 3.65-3.60 (m, 4H), 3.58-3.51 (m, 4H); MH+ 401.

Examples 2-17

The following compounds were prepared by the procedure of Example 1 using the appropriate starting materials.

| Ex | Compound | NMR | M/z | SM |
|---|---|---|---|---|
| 2 | [4-(4-Imidazo[1,2-a]pyridin-3-yl-pyrimidin-2-ylamino)-phenyl]-(4-methyl-piperazin-1-yl)-methanone | (400.132 MHz) 10.12 (d, 1H), 9.89 (s, 1H), 8.63 (s, 1H), 8.48 (d, 1H), 7.84 (d, 2H), 7.78 (d, 1H), 7.52 (t, 1H), 7.46 (d, 1H), 7.40 (d, 2H), 7.15 (t, 1H), 3.58-3.48 (m, 4H), 2.38-2.30 (m, 4H), 2.21 (s, 3H) | 414 | 4-Imidazo[1,2-a]pyridin-3-yl-pyrimidin-2-ylamine[1] and Example 59 of WO 03/004472 |
| 3 | [4-(4-Imidazo[1,2-a]pyridin-3-yl-pyrimidin-2- | (400.132 MHz) 10.09 (d, 1H), 9.73 (s, 1H), 8.62 (s, 1H), 8.46 (d, 1H), 7.77 (d, 1H), 7.66 (s, | 428 | 4-Imidazo[1,2-a]pyridin-3-yl-pyrimidin-2- |

-continued

| Ex | Compound | NMR | M/z | SM |
|---|---|---|---|---|
|  | ylamino)-2-methyl-phenyl]-(4-methyl-piperazin-1-yl)-methanone | 1H), 7.62 (d, 1H), 7.50 (t, 1H), 7.42 (d, 1H), 7.13-7.09 (m, 2H), 3.71-3.62 (m, 2H), 3.25-3.17 (m, 2H), 2.41-2.31 (m, 2H), 2.27-2.24 (m, 5H), 2.19 (s, 3H) |  | ylamine[1] and Method 1 |
| 4 | [2-Fluoro-4-(4-imidazo[1,2-a]pyridin-3-yl-pyrimidin-2-ylamino)-phenyl]-(4-methyl-piperazin-1-yl)-methanone | (400.132 MHz) 10.10 (d, 1H), 10.05 (s, 1H), 8.63 (s, 1H), 8.50 (d, 1H), 7.92 (d, 1H), 7.78 (d, 1H), 7.55-7.48 (m, 3H), 7.34 (t, 1H), 7.15 (t, 1H), 3.68-3.60 (m, 2H), 3.33-3.27 (m, 2H), 2.41-2.23 (m, 4H), 2.20 (s, 3H) | 432 | 4-Imidazo[1,2-a]pyridin-3-yl-pyrimidin-2-ylamine[1] and Method 2 |
| 5 | [4-(4-Imidazo[1,2-a]pyridin-3-yl-pyrimidin-2-ylamino)-2-methyl-phenyl]-morpholin-4-yl-methanone | (400.132 MHz) 10.04 (d, 1H), 9.71 (s, 1H), 8.57 (s, 1H), 8.40 (d, 1H), 7.72 (d, 1H), 7.61 (s, 1H), 7.57 (d, 1H), 7.45 (t, 1H), 7.37 (d, 1H), 7.10 (d, 1H), 7.06 (t, 1H), 3.63-3.55 (m, 4H), 3.50-3.43 (m, 2H), 3.19-3.12 (m, 2H), 2.18 (s, 3H) | 415 | 4-Imidazo[1,2-a]pyridin-3-yl-pyrimidin-2-ylamine[1] and Method 3 |
| 6 | [2-Fluoro-4-(4-imidazo[1,2-a]pyridin-3-yl-pyrimidin-2-ylamino)-phenyl]-morpholin-4-yl-methanone | (400.132 MHz) 10.07 (s, 1H), 10.04 (s, 1H), 8.60 (s, 1H), 8.46 (d, 1H), 7.88 (d, 1H), 7.73 (d, 1H), 7.49-7.45 (m, 3H), 7.32 (t, 1H), 7.11 (t, 1H), 3.61-3.56 (m, 4H), 3.53-3.47 (m, 2H), 3.28-3.24 (m, 2H) | 419 | 4-Imidazo[1,2-a]pyridin-3-yl-pyrimidin-2-ylamine[1] and Method 4 |
| 7 | ((S)-3-Dimethylamino-pyrrolidin-1-yl)-[4-(4-imidazo[1,2-a]pyridin-3-yl-pyrimidin-2-ylamino)-phenyl]-methanone | (400.132 MHz) 10.13 (d, 1H), 9.89 (s, 1H), 8.63 (s, 1H), 8.48 (d, 1H), 7.84 (d, 2H), 7.78 (d, 1H), 7.59-7.48 (m, 3H), 7.46 (d, 1H), 7.15 (t, 1H), 3.71-3.46 (m, 3H), 3.38-3.24 (m, 1H), 2.75-2.60 (m, 1H), 2.18 (s, 3H), 2.12 (s, 3H), 2.08-2.00 (m, 1H), 1.80-1.66 (m, 1H) | 429 | 4-Imidazo[1,2-a]pyridin-3-yl-pyrimidin-2-ylamine[1] and Method 9 |
| 8 | ((S)-3-Dimethylamino-pyrrolidin-1-yl)-[2-fluoro-4-(4-imidazo[1,2-a]pyridin-3-yl-pyrimidin-2-ylamino)-phenyl]-methanone | (400.132 MHz) 10.11 (d, 1H), 10.05 (s, 1H), 8.65 (s, 1H), 8.52 (d, 1H), 7.95-7.90 (d of d, 1H), 7.79 (d, 1H), 7.55-7.50 (m, 3H), 7.42-7.36 (m, 1H), 7.17 (t, 1H), 3.75-3.61 (m, 1H), 3.48-3.14 (m, 3H under H$_2$O), 2.79-2.67 (m, 1H), 2.19 (s, 3H), 2.11-1.99 (m, 4H), 1.82-1.68 (m, 1H) | 446 | 4-Imidazo[1,2-a]pyridin-3-yl-pyrimidin-2-ylamine[1] and Method 5 |
| 9 | ((S)-3-Dimethylamino-pyrrolidin-1-yl)-[4-(4-imidazo[1,2-a]pyridin-3-yl-pyrimidin-2-ylamino)-2-methyl-phenyl]-methanone | (400.132 MHz) 10.10 (d, 1H), 9.71 (s, 1H), 8.62 (s, 1H), 8.47 (d, 1H), 7.78 (d, 1H), 7.67-7.60 (m, 2H), 7.51 (t, 1H), 7.43 (d, 1H), 7.19 (t, 1H), 7.13 (t, 1H), 3.78-3.63 (m, 1H), 3.47-3.00 (m, 3H under H$_2$O), 2.78-2.68 (m, 1H), 2.25 (d, 3H), 2.20 (s, 3H), 2.09 (s, 3H), 2.05-1.97 (m, 1H), 1.82-1.68 (m, 1H) | 442 | 4-Imidazo[1,2-a]pyridin-3-yl-pyrimidin-2-ylamine[1] and Method 6 |
| 10 | ((R)-3-Dimethylamino-pyrrolidin-1-yl)-[4-(4-imidazo[1,2-a]pyridin-3-yl-pyrimidin-2-ylamino)-phenyl]-methanone | (400.132 MHz) 10.13 (d, 1H), 9.89 (s, 1H), 8.63 (s, 1H), 8.49 (d, 1H), 7.85-7.77 (m, 3H), 7.56-7.45 (m, 4H), 7.16 (t, 1H), 3.74-3.20 (m, 4H), 2.75-2.61 (m, 1H), 2.23-1.98 (m, 7H), 1.79-1.67 (m, 1H) | 428 | 4-Imidazo[1,2-a]pyridin-3-yl-pyrimidin-2-ylamine[1] and Method 10 |
| 11 | ((R)-3-Dimethylamino-pyrrolidin-1-yl)-[2-fluoro-4-(4-imidazo[1,2-a]pyridin-3-yl- | NMR (400.132 MHz) 10.12 (d, 1H), 10.06 (d, 1H), 8.65 (s, 1H), 8.52 (d, 1H), 7.95-7.91 (m, 1H), 7.80 (d, 1H), 7.55-7.50 (m, 3H), 7.42-7.37 (m, 1H), 7.18 (t, 1H), | 447 | 4-Imidazo[1,2-a]pyridin-3-yl-pyrimidin-2-ylamine[1] and Method 7 |

-continued

| Ex | Compound | NMR | M/z | SM |
|---|---|---|---|---|
|  | pyrimidin-2-ylamino)-phenyl]-methanone | 3.75-3.61 (m, 1H), 3.48-3.34 (m, 2H), 3.24-3.14 (m, 1H), 2.77-2.67 (m, 1H), 2.19 (s, 3H), 2.11-1.99 (m, 4H), 1.82-1.67 (m, 1H) |  |  |
| 12 | ((R)-3-Dimethylamino-pyrrolidin-1-yl)-[4-(4-imidazo[1,2-a]pyridin-3-yl-pyrimidin-2-ylamino)-2-methyl-phenyl]-methanone | NMR (400.132 MHz) 10.10 (d, 1H), 9.72 (s, 1H), 8.62 (s, 1H), 8.47 (d, 1H), 7.78 (d, 1H), 7.67-7.60 (m, 2H), 7.51 (t, 1H), 7.43 (d, 1H), 7.19 (t, 1H), 7.13 (t, 1H), 3.77-3.63 (m, 1H), 3.47-3.00 (m, 3H), 2.71 (septet, 1H), 2.25 (d, 3H), 2.19 (s, 3H), 2.08-1.95 (m, 4H), 1.81-1.67 (m, 1H) | 443 | 4-Imidazo[1,2-a]pyridin-3-yl-pyrimidin-2-ylamine[1] and Method 8 |
| 13 | [4-(4-Imidazo[1,2-a]pyridin-3-yl-pyrimidin-2-ylamino)-phenyl]-(4-methyl-[1,4]diazepan-1-yl)-methanone | NMR (499.803 MHz) 9.99 (d, 1H), 9.45 (s, 1H), 8.49 (s, 1H), 8.45 (d, 1H), 7.78 (d, 2H), 7.72 (d, 1H), 7.46 (t, 1H), 7.37-7.34 (m, 3H), 7.07 (t, 1H), 3.60-3.54 (m, 4H), 2.62 (t, 2H), 2.58 (t, 2H), 2.31 (s, 3H), 1.81 (quintet, 2H) | 428 | 4-Imidazo[1,2-a]pyridin-3-yl-pyrimidin-2-ylamine[1] and Method 11 |
| 14 | {4-[4-(2-Methyl-imidazo[1,2-a]pyridin-3-yl)-pyrimidin-2-ylamino]-phenyl}-(4-methyl-piperazin-1-yl)-methanone | NMR (400.132 MHz) 9.87 (s, 1H), 9.78 (d, 1H), 8.57 (d, 1H), 7.84 (m, 2H), 7.65 (d, 1H), 7.45 (m, 1H), 7.37 (d, 2H), 7.16 (d, 1H), 7.04 (m, 1H), 3.52 (m, 4H), 2.67 (s, 3H), 2.33 (m, 4H), 2.21 (s, 3H) | 428 | 4-(2-Methyl-imidazo[1,2-a]pyridin-3-yl)-pyrimidin-2-ylamine[1]; Example 59 of WO 03/004472 |
| 15 | (4-Methyl-[1,4]diazepan-1-yl)-{4-[4-(2-methyl-imidazo[1,2-a]pyridin-3-yl)-pyrimidin-2-ylamino]-phenyl}-methanone | (499.803 MHz, 373K) 9.65 (d, 1H), 9.44 (s, 1H), 8.54 (d, 1H), 7.40 (m, 1H), 7.79 (m, 2H), 7.59 (d, 1H), 7.33 (d, 2H), 7.12 (d, 1H), 6.97 (t, 1H), 3.56 (m, 4H), 2.66 (s, 3H), 2.62 (m, 2H), 2.57 (m, 2H), 2.31 (s, 3H), 1.81 (m, 2H) | 442 | 4-(2-Methyl-imidazo[1,2-a]pyridin-3-yl)-pyrimidin-2-ylamine[1], Method 11 |
| 16 | ((S)-3-Dimethylamino-pyrrolidin-1-yl)-{4-[4-(2-methyl-imidazo[1,2-a]pyridin-3-yl)-pyrimidin-2-ylamino]-phenyl}-methanone | (499.803 MHz, 373K) 9.65 (d, 1H), 9.47 (s, 1H), 8.54 (d, 1H), 7.81 (m, 2H), 7.59 (d, 1H), 7.48 (m, 2H), 7.40 (m, 1H), 7.13 (d, 1H), 6.97 (t, 1H), 3.59-3.68 (m, 2H), 3.50 (m, 1H), 3.34 (m, 1H), 2.84 (m, 1H), 2.67 (s, 3H), 2.21 (s, 6H), 2.04 (m, 1H), 1.79 (m, 1H) | 442 | 4-(2-Methyl-imidazo[1,2-a]pyridin-3-yl)-pyrimidin-2-ylamine[1]; Method 9 |
| 17 | (4-Isopropyl-[1,4]diazepan-1-yl)-{4-[4-(2-methyl-imidazo[1,2-a]pyridin-3-yl)-pyrimidin-2-ylamino]-phenyl}-methanone | (499.803 MHz, 373K) 9.65 (d, 1H) 9.43 (s, 1H), 8.53 (d, 1H), 7.79 (m, 2H), 7.59 (d, 1H), 7.32 (d, 2H), 7.40 (m, 1H), 7.12 (d, 1H), 6.96 (t, 1H), 3.54 (m, 4H), 2.88 (m, 1H), 2.62-2.70 (m, 7H), 1.73 (m, 2H), 0.98 (d, 6H) | 470 | 4-(2-Methyl-imidazo[1,2-a]pyridin-3-yl)-pyrimidin-2-ylamine[1]; Method 12 |

[1] Bioorganic & Medicinal Chemistry Letters 2004, 14(9), 2245-2248

Preparation of Starting Materials

Method 1

(4-Bromo-2-methyl-phenyl)-(4-methyl-piperazin-1-yl)-methanone

4-Bromo-2-methylbenzoic acid (10 g, 46.5 mmol), and HBTU (23 g, 60.5 mmol) were dissolved in DMF (150 mL), then N-methyl piperazine (6.0 g, 60.5 mmol) and DIPEA (21 mL, 121 mmol) were added. The reaction was stirred overnight before the removal of the DMF in vacuo, the gum was quenched with 2.0N NaOH (100 mL), extracted with diethyl ether (3×200 mL), dried (MgSO$_4$) and solvent removed in vacuo to yield a viscous gum. Purification on silica using 0-10% MeOH in DCM as eluent, gave the title compound as viscous oil. The oil was dissolved in the minimum amount of diethyl ether, iso-hexane was added to give a colourless solid which was filtered and dried (11.8 g, 86%); $^1$H NMR (CDCl$_3$) 7.40 (s, 1H), 7.36 (d, 1H), 7.04 (d, 1H), 3.86-3.79 (m, 2H), 3.27-3.21 (m, 2H), 2.51-2.45 (m, 2H), 2.32-2.29 (m, 8H); MH+ 298.

Methods 2-8

Using the procedure described for Method 1 the following Methods 2-8 were prepared in a similar way.

| Meth | Compound | NMR | M/z | SM |
|---|---|---|---|---|
| 2 | (4-Bromo-2-fluoro-phenyl)-(4-methyl-piperazin-1-yl)-methanone | (CDCl$_3$) 7.35 (d, 1H), 7.33-7.22 (m, 2H), 3.86-3.79 (m, 2H), 3.27-3.21 (m, 2H), 2.51-2.45 (m, 2H), 2.32-2.29 (m, 8H) | 301 | 4-bromo-2-fluorobenzoic acid, N-methylpiperazine |
| 3 | (4-Bromo-2-methyl-phenyl)-morpholin-4-yl-methanone | (CDCl$_3$) 7.40 (s, 1H), 7.36 (d, 1H), 7.04 (d, 1H), 3.83-3.73 (m, 4H), 3.61-3.56 (m, 2H), 3.26-3.20 (m, 2H), 2.30 (s, 3H) | 285 | 4-Bromo-2-methylbenzoic acid, morpholine |
| 4 | (4-Bromo-2-fluoro-phenyl)-morpholin-4-yl-methanone | (CDCl$_3$) 7.40 (d, 1H), 7.33-7.31 (m, 1H), 7.30-7.26 (m, 1H), 3.87-3.74 (m, 4H), 3.67-3.58 (m, 2H), 3.40-3.29 (m, 2H) | 289 | 4-bromo-2-fluorobenzoic acid, morpholine |
| 5 | (3S)-1-(4-Bromo-2-fluorobenzoyl)-N,N-dimethylpyrrolidin-3-amine | (CDCl$_3$) 7.38-7.27 (m, 3H), 3.98-3.81 (m, 1H), 3.63-3.17 (m, 3H), 2.85-2.68 (m, 1H), 2.30 (s, 3H), 2.21 (s, 3H), 2.19-2.04 (m, 1H), 1.92-1.77 (m, 1H) | 316 | (3S)-N,N-dimethylpyrrolidin-3-amine and 4-bromo-2-fluorobenzoic acid |
| 6 | (3S)-1-(4-Bromo-2-methylbenzoyl)-N,N-dimethylpyrrolidin-3-amine | (CDCl$_3$) 7.39 (s, 1H), 7.35 (d, 1H), 7.06 (d, 1H), 4.00-3.84 (m, 1H), 3.61-3.35 (m, 1H), 3.31-3.23 (m, 1H), 3.18-2.95 (m, 1H), 2.80-2.63 (m, 1H), 2.29 (s, 6H), 2.19-2.03 (m, 4H), 1.90-1.74 (m, 1H); m/z 312. | 312 | (3S)-N,N-dimethylpyrrolidin-3-amine and 4-bromo-2-methylbenzoic acid |
| 7 | (3R)-1-(4-Bromo-2-fluorobenzoyl)-N,N-dimethylpyrrolidin-3-amine | (CDCl$_3$) 7.38-7.27 (m, 3H), 3.97-3.81 (m, 1H), 3.63-3.17 (m, 3H), 2.84-2.68 (m, 1H), 2.30 (s, 3H), 2.21 (s, 3H), 2.17-2.02 (m, 1H), 1.90-1.77 (m, 1H) | 316 | (3R)-N,N-dimethylpyrrolidin-3-amine and 4-bromo-2-fluorobenzoic acid |
| 8 | (3R)-1-(4-Bromo-2-methylbenzoyl)-N,N-dimethylpyrrolidin-3-amine | 300.072 MHz, CDCl$_3$) 7.39 (s, 1H), 7.35 (d, 1H), 7.07 (dd, 1H), 4.00-3.84 (m, 1H), 3.61-3.35 (m, 1H), 3.31-2.95 (m, 2H), 2.81-2.64 (m, 1H), 2.30 (s, 6H), 2.19-2.02 (m, 4H), 1.90-1.76 (m, 1H) | 312 | (3R)-N,N-dimethylpyrrolidin-3-amine and 4-bromo-2-methylbenzoic acid |

Method 9

((S)-3-Dimethylamino-pyrrolidin-1-yl)-(4-iodo-phenyl)-methanone

4-Iodobenzoyl chloride (5 g, 0.019 mol) and triethylamine (6.6 ml, 0.048 mol) were added to DCM (100 ml) and cooled to 0° C. To this was slowly added (S)-dimethylamino-pyrrolidine (2.2 g, 0.019 mol), the reaction was stirred for 1 hour then the solvent was removed in vacuo to 90% volume. The slurry obtained was quenched with 2.0 M NaOH (50 ml), extracted with diethyl ether (3×200 ml), dried (MgSO$_4$) and the solvent removed in vacuo to yield a yellow solid. Diethyl ether was added and the system was sonicated for 10 minutes and filtered to give the title compound as an off white solid (3.9 g, 60%); $^1$H NMR (300.072 MHz, CDCl$_3$) 7.75 (d, 2H), 7.25 (d, 2H), 3.94-3.78 (m, 1H), 3.66-3.25 (m, 3H), 2.81-2.62 (m, 1H), 2.30 (s, 3H), 2.21 (s, 3H), 2.16-2.02 (m, 1H), 1.97-1.76 (m, 1H); MH+ 345.

Methods 10-12

Using the procedure described for Method 9 the following Methods 10-12 were prepared in a similar way.

| Meth | Compound | NMR | M/z | SM |
|---|---|---|---|---|
| 10 | ((R)-3-Dimethylamino-pyrrolidin-1-yl)-(4-iodo-phenyl)-methanone | (CDCl$_3$) 7.75 (d, 2H), 7.25 (d, 2H), 3.94-3.78 (m, 1H), 3.66-3.25 (m, 3H), 2.81-2.62 (m, 1H), 2.30 (s, 3H), 2.21 (s, 3H), 2.16-2.02 (m, 1H), 1.97-1.76 (m, 1H); | 345 | 4-iodobenzoyl chloride and (R)-dimethylamino pyrrolidine |
| 11 | 1-(4-Iodobenzoyl)-4-methyl-1,4-diazepane | (CDCl$_3$) 7.79 (d, 2H), 7.18 (d, 2H), 3.84-3.79 (m, 2H), 3.54-3.52 (m, 1H), 3.48 (t, 1H), 2.79-2.77 (m, 1H), 2.70-2.66 (m, 1H), 2.62-2.55 (m, 2H), 2.45 (s, 3H), 2.07-2.00 (m, 1H), 1.91-1.84 (m, 1H) | 345 | N-methylhomopiperazine and 4-iodobenzoyl chloride |

-continued

| Meth | Compound | NMR | M/z | SM |
|---|---|---|---|---|
| 12 | 1-Benzoyl-4-isopropyl-1,4-diazepane | (CDCl$_3$) 7.74 (d, 2H), 7.13 (d, 2H), 3.75-3.72 (m, 2H), 3.40 (t, 2H), 2.96-2.84 (m, 1H), 2.79-2.77 (m, 1H), 2.67 (t, 1H), 2.62-2.56 (m, 2H), 1.92-1.87 (m, 1H), 1.71-1.67 (m, 1H), 1.03-0.97 (m, 6H) | 373 | 1-isopropyl-1,4-diazepane (Method 13) and 4-iodobenzoyl chloride |

Method 13

1-Isopropyl-1,4-diazepane tert-Butyl 1,4-diazepane-1-carboxylate (17 g) and acetone (10 g) were added to MeOH (150 mL) and stirred at 0° C. for 20 mins. NaCNBH$_3$ (6.4 g) was slowly added over a 20-minute period keeping the temperature below 0° C. After complete addition the reaction was allowed to warm to ambient temperature and stirred for 56 hrs. The reaction was concentrated in vacuo to yield a yellow residue. This was quenched with water (100 mL), extracted with ether (3×100 mL), dried and the solvent removed in vacuo to yield a viscous clear oil (20 g). The oil was added to TFA (50 mL) and DCM (50 mL), the reaction was stirred for 16 hrs before concentration in vacuo. The reaction was quenched with water (30 mL), to this was added potassium carbonate until the aqueous was fully saturated, this was then extracted with EtOAc (3×200 mL), dried and the solvent carefully removed in vacuo to yield the title compound as a yellow oil (5.2 g); NMR (400.132 MHz, CDCl$_3$) 2.94-2.86 (m, 5H), 2.68-2.63 (m, 4H), 1.74-1.68 (m, 2H), 1.01 (d, 6H).

Example 18

The following illustrate representative pharmaceutical dosage forms containing the compound of formula (I), or a pharmaceutically acceptable salt or in vivo hydrolysable ester thereof (hereafter compound X), for therapeutic or prophylactic use in humans:—

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b): Tablet II | |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c): Tablet III | |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

-continued

| (d): Capsule | mg/capsule |
|---|---|
| Compound X | 10 |
| Lactose Ph.Eur | 488.5 |
| Magnesium stearate | 1.5 |
| (e): Injection I | (50 mg/ml) |
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |
| (f): Injection II | 10 mg/ml |
| Compound X | 1.0% w/v |
| Sodium phosphate BP | 3.6% w/v |
| 0.1 M Sodium hydroxide solution | 15.0% v/v |
| Water for injection | to 100% |
| (g): Injection III | (1 mg/ml, buffered to pH6) |
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)-(c) may be enteric coated by conventional means, for example to provide a coating of cellulose acetate phthalate.

The invention claimed is:
1. A compound of formula (I):

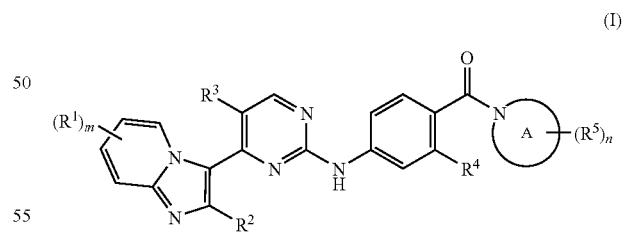

(I)

wherein:
R$^1$ is selected from halo, amino, C$_{1-3}$alkyl, C$_{1-3}$alkoxy, N—(C$_{1-3}$alkyl)amino, N,N—(C$_{1-3}$alkyl)$_2$amino and a nitrogen linked 4-7 membered saturated ring which optionally contains an additional nitrogen, oxygen or sulphur atom;
m is 0-4; wherein the values of R$^1$ may be the same or different;
R$^2$ is selected from hydrogen, halo, amino, C$_{1-3}$alkyl and C$_{1-3}$alkoxy;

$R^3$ is hydrogen or halo;

$R^4$ is hydrogen, ethynyl, halo, cyano, hydroxy, amino, mesyl, trifluoromethyl, trifluoromethoxy, methyl, ethyl or methoxy;

Ring A is a nitrogen linked 4-7 membered saturated ring which optionally contains an additional nitrogen, oxygen or sulphur atom; wherein if said ring contains an additional nitrogen atom that nitrogen may be optionally substituted by $R^6$;

$R^5$ is a substituent on carbon and is selected from halo, cyano, hydroxy, trifluoromethoxy, amino, carboxy, carbamoyl, sulphamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl; wherein $R^5$ independently may be optionally substituted on carbon by one or more $R^7$; or $R^5$ is —NHR$^8$, —NR$^9$R$^{10}$ or —O—R$^{11}$;

n is 0-4; wherein the values of $R^5$ may be the same or different;

$R^6$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl and N,N—($C_{1-6}$alkyl)carbamoyl; wherein $R^6$ may be optionally substituted on carbon by one or more $R^{12}$;

$R^8$, $R^9$, $R^{10}$ $R^{11}$ are independently selected from $C_{1-4}$alkyl, $C_{1-4}$alkanoyl, $C_{1-4}$alkylsulphonyl, $C_{2-4}$alkenylsulphonyl, $C_{2-4}$alkynylsulphonyl, $C_{1-4}$alkoxycarbonyl, carbamoyl, N—($C_{1-4}$alkyl)carbamoyl, N,N—($C_{1-4}$alkyl)carbamoyl, carbocyclyl and heterocyclyl; wherein $R^8$, $R^9$, $R^{10}$ and $R^{11}$ may be independently optionally substituted on carbon by a group selected from $R^{13}$; and wherein if said heterocyclyl contains an —NH— moiety that nitrogen may be optionally substituted by $R^{14}$;

$R^{13}$ is selected from halo, cyano, hydroxy, amino, trifluoromethyl, trifluoromethoxy, $C_{1-3}$alkyl and $C_{1-3}$alkoxy;

$R^{14}$ is selected from $C_{1-3}$alkyl, $C_{1-3}$alkanoyl, $C_{1-3}$alkylsulphonyl, $C_{1-3}$alkoxycarbonyl, carbamoyl, N—($C_{1-3}$alkyl)carbamoyl and N,N—($C_{1-3}$alkyl)carbamoyl; and $R^7$ and $R^{12}$ are independently selected from halo, cyano, hydroxy, trifluoromethoxy, trifluoromethyl, amino, carboxy, carbamoyl, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl;

or a pharmaceutically acceptable salt thereof.

2. The compound of formula (I), or a pharmaceutically acceptable salt thereof, as claimed in claim 1, wherein m is 0.

3. The compound of formula (I), or a pharmaceutically acceptable salt thereof, as claimed in claim 1, wherein $R^2$ is selected from hydrogen or $C_{1-3}$alkyl.

4. The compound of formula (I), or a pharmaceutically acceptable salt thereof, as claimed in claim 1 wherein $R^3$ is hydrogen.

5. The compound of formula (I), or a pharmaceutically acceptable salt thereof, as claimed in claim 1 wherein $R^4$ is hydrogen, halo or methyl.

6. The compound of formula (I), or a pharmaceutically acceptable salt thereof, as claimed in claim 1 wherein Ring A is a nitrogen linked 5-7 membered saturated ring which optionally contains an additional nitrogen or oxygen atom; wherein if said ring contains an additional nitrogen atom that nitrogen may be optionally substituted by $R^6$; wherein $R^6$ is $C_{1-6}$alkyl.

7. The compound of formula (I), or a pharmaceutically acceptable salt thereof, as claimed in claim 1 wherein $R^5$ is a substituent on carbon and is selected from —NR$^9$R$^{10}$; wherein $R^9$ and $R^{10}$ are independently selected from $C_{1-4}$alkyl.

8. The compound of formula (I), or a pharmaceutically acceptable salt thereof, as claimed in claims 1 wherein:

n is 0 or 1.

9. A compound of formula (I):

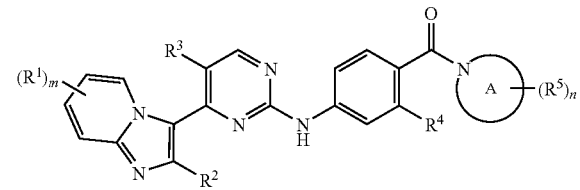

wherein m is 0;

$R^2$ is selected from hydrogen or methyl;

$R^3$ is hydrogen;

$R^4$ is hydrogen, fluoro or methyl;

Ring A is pyrrolidin-1-yl, 4-methylpiperazin-1-yl, 4-methylhomopiperazin-1-yl or 4-isopropylhomopiperazin-1-yl or morpholino;

$R^5$ is a substituent on carbon and is dimethylamino;

n is 0 or 1;

or a pharmaceutically acceptable salt thereof.

10. A compound of formula (I):

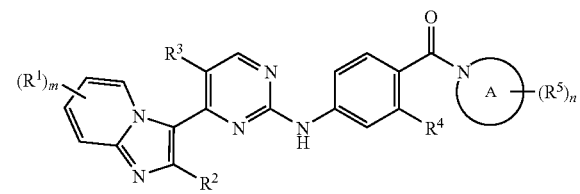

selected from:
- [4-(4-imidazo[1,2-a]pyridin-3-yl-pyrimidin-2-ylamino)-phenyl]-morpholin-4-yl-methanone;
- [4-(4-imidazo[1,2-a]pyridin-3-yl-pyrimidin-2-ylamino)-phenyl]-(4-methyl-piperazin-1-yl)-methanone;
- [4-(4-imidazo[1,2-a]pyridin-3-yl-pyrimidin-2-ylamino)-2-methyl-phenyl]-(4-methyl-piperazin-1-yl)-methanone;
- [2-fluoro-4-(4-imidazo[1,2-a]pyridin-3-yl-pyrimidin-2-ylamino)-phenyl]-(4-methyl-piperazin-1-yl)-methanone;
- [4-(4-imidazo[1,2-a]pyridin-3-yl-pyrimidin-2-ylamino)-2-methyl-phenyl]-morpholin-4-yl-methanone;
- [2-fluoro-4-(4-imidazo[1,2-a]pyridin-3-yl-pyrimidin-2-ylamino)-phenyl]-morpholin-4-yl-methanone;
- ((S)-3-dimethylamino-pyrrolidin-1-yl)-[4-(4-imidazo[1,2-a]pyridin-3-yl-pyrimidin-2-ylamino)-phenyl]-methanone;

((S)-3-dimethylamino-pyrrolidin-1-yl)-[2-fluoro-4-(4-imidazo[1,2-a]pyridin-3-yl-pyrimidin-2-ylamino)-phenyl]-methanone;

((S)-3-dimethylamino-pyrrolidin-1-yl)-[4-(4-imidazo[1,2-a]pyridin-3-yl-pyrimidin-2-ylamino)-2-methyl-phenyl]-methanone;

((R)-3-dimethylamino-pyrrolidin-1-yl)-[4-(4-imidazo[1,2-a]pyridin-3-yl-pyrimidin-2-ylamino)-phenyl]-methanone;

((R)-3-dimethylamino-pyrrolidin-1-yl)-[2-fluoro-4-(4-imidazo[1,2-a]pyridin-3-yl-pyrimidin-2-ylamino)-phenyl]-methanone;

((R)-3-dimethylamino-pyrrolidin-1-yl)-[4-(4-imidazo[1,2-a]pyridin-3-yl-pyrimidin-2-ylamino)-2-methyl-phenyl]-methanone;

[4-(4-imidazo[1,2-a]pyridin-3-yl-pyrimidin-2-ylamino)-phenyl]-(4-methyl-[1,4]diazepan-1-yl)-methanone;

{4-[4-(2-methyl-imidazo[1,2-a]pyridin-3-yl)-pyrimidin-2-ylamino]-phenyl}-(4-methyl-piperazin-1-yl)-methanone;

(4-methyl-[1,4]diazepan-1-yl)-{4-[4-(2-methyl-imidazo[1,2-a]pyridin-3-yl)-pyrimidin-2-ylaminol]-phenyl}-methanone;

((S)-3-dimethylamino-pyrrolidin-1-yl)-{4-[4-(2-methyl-imidazo[1,2-a]pyridin-3-yl)-pyrimidin-2-ylamino]-phenyl}-methanone; and (4-isopropyl-[1,4]diazepan-1-yl)-{4-[4-(2-methyl-imidazo[1,2-a]pyridin-3-yl)-pyrimidin-2-ylamino]-phenyl}-methanone;

or a pharmaceutically acceptable salt thereof.

11. The compound of formula (I), or a pharmaceutically acceptable salt thereof, as claimed in claim 1, wherein:

m is 0;

$R^2$ is selected from hydrogen or $C_{1-3}$alkyl;

$R^3$ is hydrogen;

$R^4$ is hydrogen, halo or methyl;

Ring A is a nitrogen linked 5-7 membered saturated ring which optionally contains an additional nitrogen or oxygen atom; wherein if said ring contains an additional nitrogen atom that nitrogen may be optionally substituted by $R^6$; wherein $R^6$ is $C_{1-6}$alkyl;

$R^5$ is a substituent on carbon and is selected from $-NR^9R^{10}$; wherein $R^9$ and $R^{10}$ are independently selected from $C_{1-4}$alkyl; and n is 0 or 1.

12. A process for preparing a compound of formula (I) or a pharmaceutically acceptable salt thereof, as claimed in claim 1, which process comprises of:

Process a) reacting of a pyrimidine of formula (II):

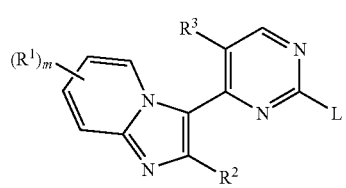

(II)

wherein L is a displaceable group; with an aniline of formula (III):

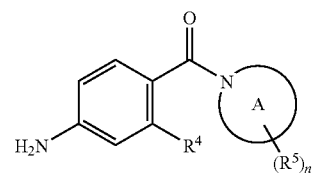

(III)

or

Process b) reacting a compound of formula (IV):

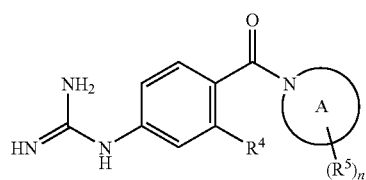

(IV)

with a compound of formula (V):

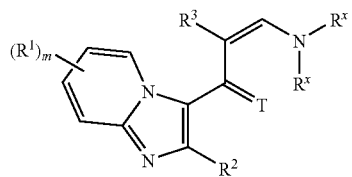

(V)

wherein T is O or S; $R^x$ may be the same or different and is selected from $C_{1-6}$alkyl; or Process c) reacting an acid of formula (VI):

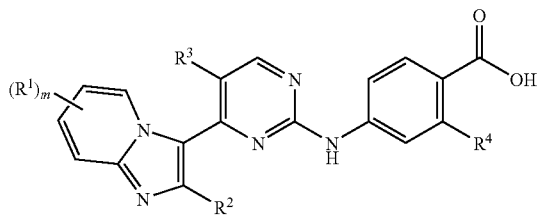

(VI)

or an activated acid derivative thereof; with an amine of formula (VII):

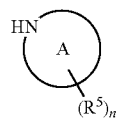

(VII)

or

Process d) for compounds of formula (I); reacting a pyrimidine of formula (VIII):

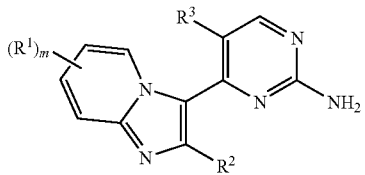
(VIII)

with a compound of formula (IX):

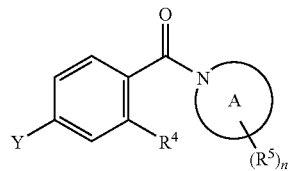
(IX)

where Y is a displaceable group;

and thereafter optionally:

i) converting a compound of the formula (I) into another compound of the formula (I);

ii) removing any protecting groups; and/or iii) forming a pharmaceutically acceptable salt.

13. A pharmaceutical composition which comprises a compound of the formula (I), or a pharmaceutically acceptable salt thereof, as claimed in claim 1, and a pharmaceutically-acceptable diluent or carrier.

14. A method of treating rheumatoid arthritis in a warm-blooded animal in need of such treatment, which comprises administering to said animal an effective amount of a compound of formula (I) or a pharmaceutically acceptable salt thereof, as claimed in claim 1.

* * * * *